(12) United States Patent
Jones et al.

(10) Patent No.: US 9,834,500 B2
(45) Date of Patent: Dec. 5, 2017

(54) CYCLOHEXANOLS AND THEIR USE IN PERFUME COMPOSITIONS

(71) Applicant: International Flavors & Fragrances Inc., New York, NY (US)

(72) Inventors: Paul D. Jones, Aberdeen, NJ (US); Richard A. Weiss, Livingston, NJ (US); Robert P. Belko, Monroe, NJ (US); Richard M. Boden, Ocean, NJ (US); Michael G. Monteleone, Hazlet, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 34 days.

(21) Appl. No.: 15/223,608

(22) Filed: Jul. 29, 2016

(65) Prior Publication Data
US 2016/0332947 A1   Nov. 17, 2016

Related U.S. Application Data

(62) Division of application No. 14/336,036, filed on Jul. 21, 2014, now Pat. No. 9,434,669.

(51) Int. Cl.
| | |
|---|---|
| *C07C 43/196* | (2006.01) |
| *C11D 3/50* | (2006.01) |
| *C11B 9/00* | (2006.01) |
| *A61K 8/34* | (2006.01) |
| *A61Q 5/00* | (2006.01) |
| *A61Q 19/10* | (2006.01) |

(52) U.S. Cl.
CPC .............. *C07C 43/196* (2013.01); *A61K 8/34* (2013.01); *A61Q 5/00* (2013.01); *A61Q 19/10* (2013.01); *C11B 9/0034* (2013.01); *C11D 3/50* (2013.01); *C07C 2601/14* (2017.05)

(58) Field of Classification Search
CPC ....... C11B 9/0034; C07C 43/00; C07C 43/02; C07C 43/20; C07C 43/174; C07C 43/196
See application file for complete search history.

(56) References Cited

U.S. PATENT DOCUMENTS 4,904,465 A * 2/1990 Maillefer .............. C07C 43/196
424/65

* cited by examiner

*Primary Examiner* — Arrie L Reuther
(74) *Attorney, Agent, or Firm* — Martin Zhang; XuFan Tseng; Elizabeth M Stover

(57) ABSTRACT

The present invention is directed to novel fragrance compounds and their unexpected advantageous use in improving, enhancing or modifying a fragrance formulation through the addition of an olfactory acceptable amount of the compounds, wherein the compounds are represented by the following formula:

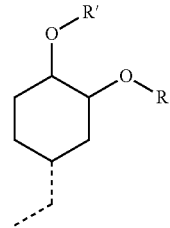

an isomer or a mixture of isomers thereof,
wherein one of R and R' represents hydrogen with the other representing a $C_1$-$C_6$ linear, branched, or cyclic alkyl, alkenyl, alkynyl or aromatic group; and
one of the dashed lines represents a carbon-carbon single bond with the other representing a carbon-carbon double bond.

7 Claims, No Drawings

CYCLOHEXANOLS AND THEIR USE IN PERFUME COMPOSITIONS

STATUS OF RELATED APPLICATIONS

This application is a divisional of U.S. Ser. No. 14/336,036, filed Jul. 21, 2014, now allowed, the content hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances.

SUMMARY OF THE INVENTION

The present invention provides novel chemicals and their unexpected advantageous use in improving, enhancing or modifying the fragrance of perfumes, colognes, toilet waters, cosmetic products, personal care products, fabric care products, cleaning products, air fresheners, and the like.

One embodiment of the present invention is directed to novel cyclohexanol compounds represented by the following formula:

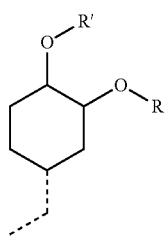

Formula I isomers or mixtures of isomers thereof,
wherein one of R and R' represents hydrogen with the other representing a $C_1$-$C_6$ linear, branched, or cyclic alkyl, alkenyl, alkynyl or aromatic group; and
one of the dashed lines represents a carbon-carbon single bond with the other representing a carbon-carbon double bond.

Another embodiment of the present invention is directed to the use of the compounds provided above as fragrance materials in perfumes, colognes, toilet waters, personal products, fabric care products, and the like.

Another embodiment of the present invention is directed to a fragrance composition comprising the compounds provided above.

Another embodiment of the present invention is directed to a fragrance product comprising the compounds provided above.

Another embodiment of the present invention is directed to a method of improving, enhancing or modifying a fragrance formulation by incorporating an olfactory acceptable amount of the compounds provided above.

These and other embodiments of the present invention will be apparent by reading the following specification.

DETAILED DESCRIPTION OF THE INVENTION

The compounds of the present invention may also be represented by ethylidene-substituted cyclohexanols of Formula II and vinyl-substituted cyclohexanols of Formula III in the following:

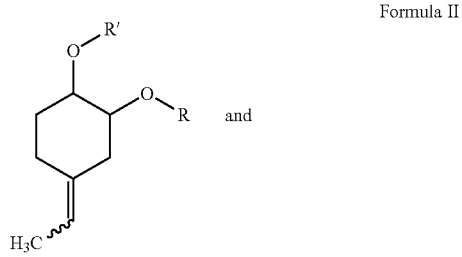

Formula II

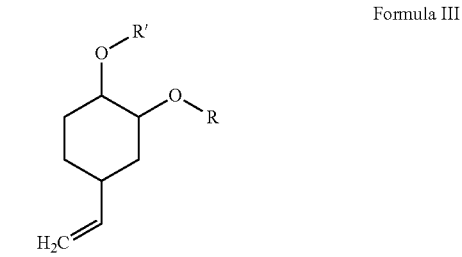

Formula III isomers or mixtures of isomers thereof,
wherein R and R' are defined as above.

The compounds of the present invention may be further represented by cyclohexanols of Formula IV in the following:

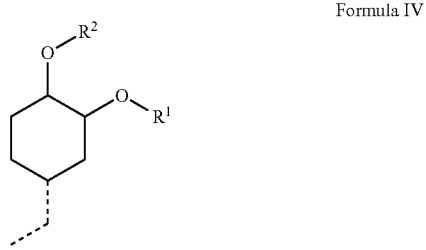

Formula IV isomers or mixtures of isomers thereof,
wherein one of $R^1$ and $R^2$ represents hydrogen with the other representing a $C_1$-$C_6$ linear, branched or cyclic alkyl group; and
one of the dashed lines represents a carbon-carbon single bond with the other representing a carbon-carbon double bond.

The cyclohexanol compounds of Formula II, III and IV may be further represented by Formula V and Formula VI in the following:

Formula V

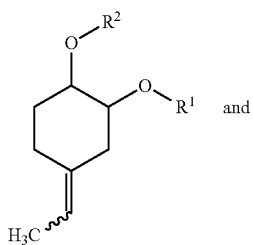

Formula VI

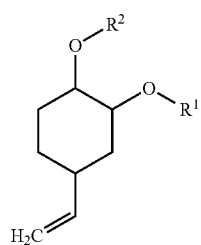

isomers or mixtures of isomers thereof,
wherein one of $R^1$ and $R^2$ are defined as above.

The novel cyclohexanols of the present invention are illustrated, for example, by following examples.

Structure 1

(E)-4-Ethylidene-2-methoxy-cyclohexanol:

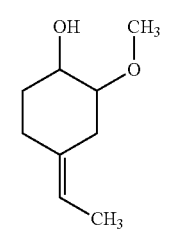

Structure 2

(Z)-4-Ethylidene-2-methoxy-cyclohexanol:

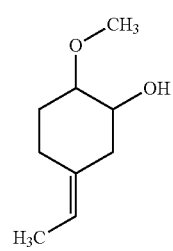

Structure 3

(E)-5-Ethylidene-2-methoxy-cyclohexanol:

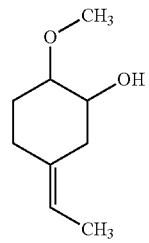

Structure 4

(Z)-5-Ethylidene-2-methoxy-cyclohexanol:

Structure 5

(E)-4-Ethylidene-2-ethoxy-cyclohexanol:

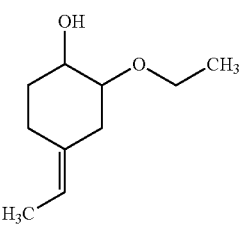

Structure 6

(Z)-4-Ethylidene-2-ethoxy-cyclohexanol:

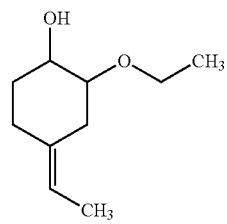

Structure 7

(E)-5-Ethylidene-2-ethoxy-cyclohexanol:

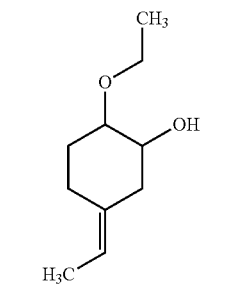

Structure 8

(Z)-5-Ethylidene-2-ethoxy-cyclohexanol:

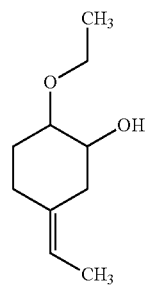

(Z)-4-Ethylidene-2-vinyloxy-cyclohexanol:

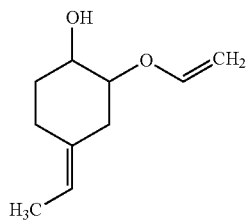

Structure 9

(Z)-4-Ethylidene-2-vinyloxy-cyclohexanol:

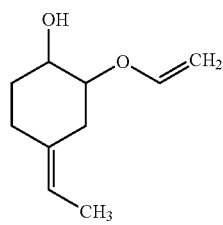

Structure 10

(E)-5-Ethylidene-2-vinyloxy-cyclohexanol:

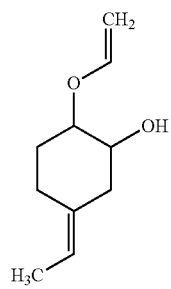

Structure 11

(Z)-5-Ethylidene-2-vinyloxy-cyclohexanol:

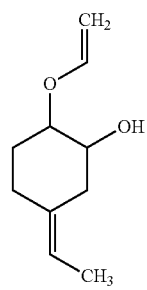

Structure 12

(E)-4-Ethylidene-2-ethynyloxy-cyclohexanol:

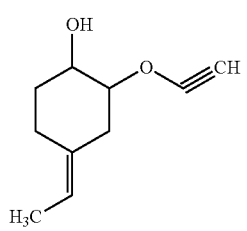

Structure 13

(Z)-4-Ethylidene-2-ethynyloxy-cyclohexanol:

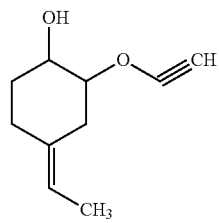

Structure 14

(E)-5-Ethylidene-2-ethynyloxy-cyclohexanol:

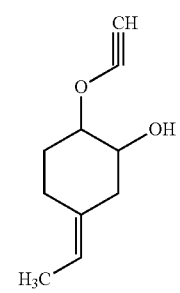

Structure 15

(Z)-5-Ethylidene-2-ethynyloxy-cyclohexanol:

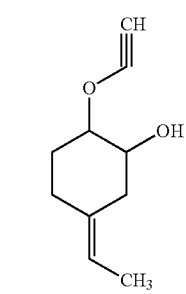

Structure 16

(E)-4-Ethylidene-2-propoxy-cyclohexanol:

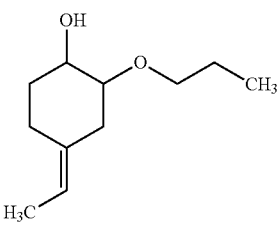

Structure 17

(Z)-4-Ethylidene-2-propoxy-cyclohexanol:

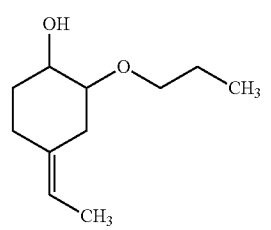

Structure 18

(E)-5-Ethylidene-2-propoxy-cyclohexanol:

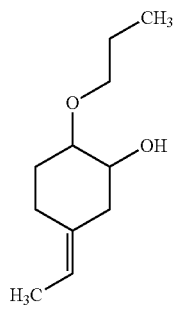

(Z)-5-Ethylidene-2-propoxy-cyclohexanol:

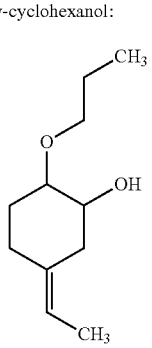

(E)-4-Ethylidene-2-isopropoxy-cyclohexanol:

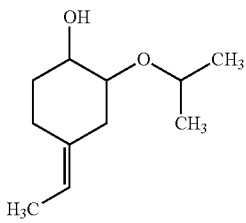

(Z)-4-Ethylidene-2-isopropoxy-cyclohexanol:

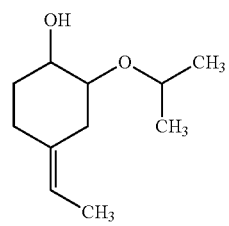

(E)-4-Ethylidene-2-isopropoxy-cyclohexanol:

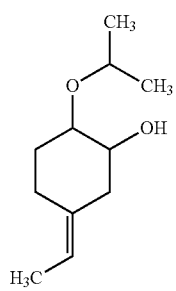

Structure 19

(Z)-5-Ethylidene-2-isopropoxy-cyclohexanol:

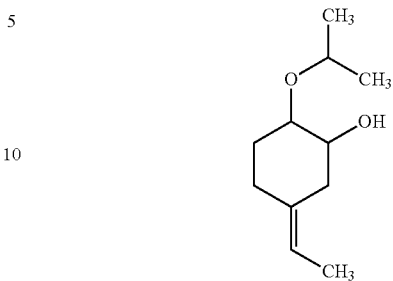

Structure 20

2-Methoxy-4-vinyl-cyclohexanol:

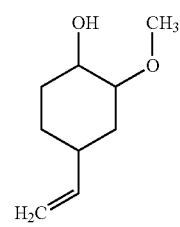

Structure 21

2-Methoxy-5-vinyl-cyclohexanol:

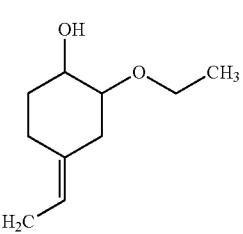

Structure 22

2-Ethoxy-4-vinyl-cyclohexanol:

Structure 23

2-Ethoxy-5-vinyl-cyclohexanol:

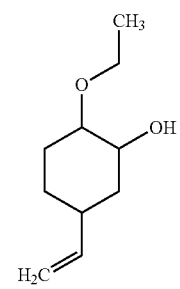

Structure 24

Structure 25

Structure 26

Structure 27

Structure 28

2-Propoxy-4-vinyl-cyclohexanol:

Structure 29

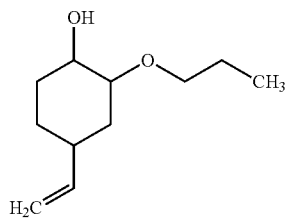

2-Propoxy-5-vinyl-cyclohexanol:

Structure 30

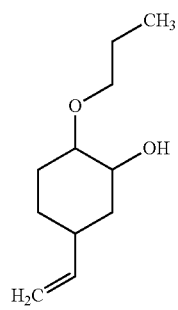

2-Allyloxy-4-vinyl-cyclohexanol:

Structure 31

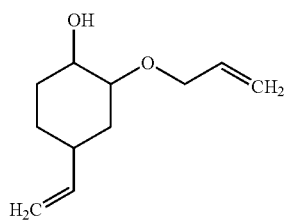

2-Allyloxy-5-vinyl-cyclohexanol:

Structure 32

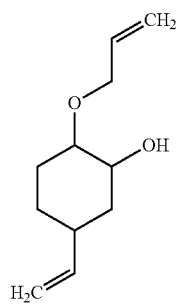

2-Prop-2-ynyloxy-4-vinyl-cyclohexanol:

Structure 33

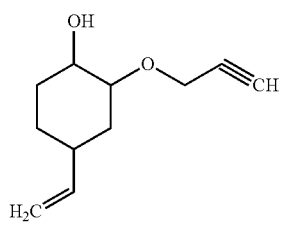

2-Prop-2-ynyloxy-5-vinyl-cyclohexanol:

Structure 34

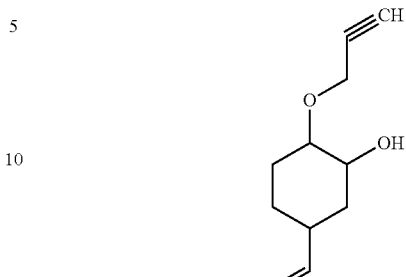

2-Isopropoxy-4-vinyl-cyclohexanol:

Structure 35

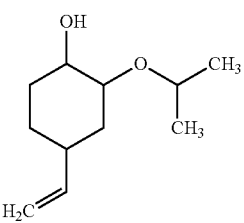

2-Isopropoxy-5-vinyl-cyclohexanol:

Structure 36

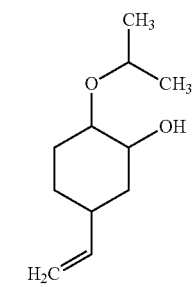

2-Butoxy-4-vinyl-cyclohexanol:

Structure 37

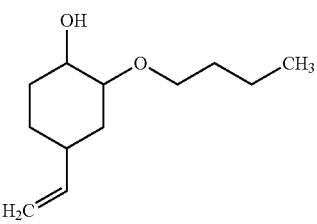

2-Butoxy-5-vinyl-cyclohexanol:

Structure 38

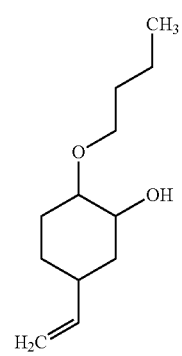

Structure 39

2-Isobutoxy-4-vinyl-cyclohexanol:

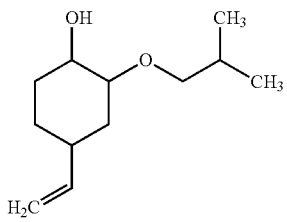

Structure 40

2-Isobutoxy-5-vinyl-cyclohexanol:

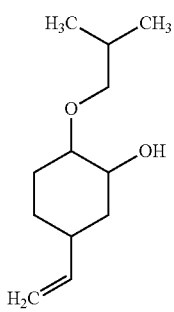

The compounds of the present invention were prepared with 3-vinyl-7-oxa-bicyclo[4.1.0]heptane according to the following reaction scheme, the details of which are specified in the Examples. Materials and catalysts were purchased from Aldrich Chemical Company unless noted otherwise.

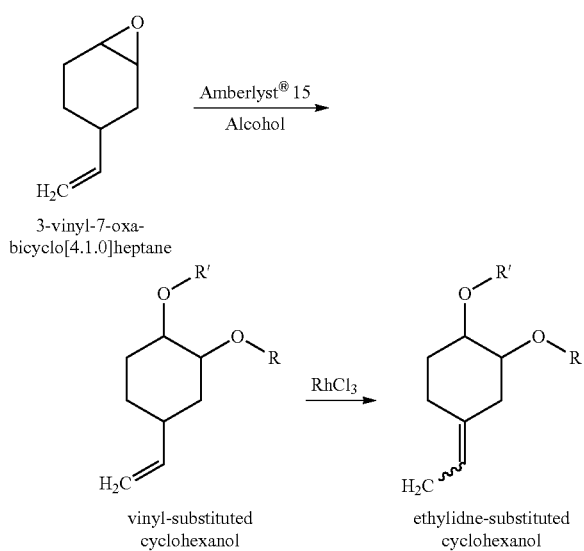

wherein $RhCl_3$ represents Rhodium(III) chloride; and R and R' are defined as above.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, particularly silica gel chromatograph, and gas chromatography trapping known as GC trapping. Yet, commercial versions of such products are mostly offered as mixtures.

The compounds of the present invention, for example, possess strong and complex sweet, spicy, woody and vanilla notes.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk; and flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The terms "fragrance formulation", "fragrance composition", and "perfume composition" are understood to mean the same and refer to a formulation that is intended for providing a fragrance character to a perfume, a cologne, toilet water, a personal product, a fabric care product, and the like. The fragrance formulation of the present invention is a composition comprising a compound of the present invention.

Olfactory acceptable amount is understood to mean the amount of a compound in a perfume composition. The compound will contribute its particular olfactory characteristics, but the olfactory effect of the perfume composition will be the sum of the effects of each of the perfumes or fragrance ingredients. Thus the compounds of the invention can be used to alter the aroma characteristics of a perfume composition, or by modifying the olfactory reaction contributed by another ingredient in the composition. The amount will vary depending on many factors including other ingredients, their relative amounts and the effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

The following are provided as specific embodiments of the present invention. Other modifications of this invention will be readily apparent to those skilled in the art. Such modifications are understood to be within the scope of this invention. The chemical materials used in the preparation of the compounds of the present invention are commercially available from Aldrich Chemical Company. As used herein all percentages are weight percent unless otherwise noted, ppm is understood to stand for parts per million, mol is understood to be mole, mmol is understood to be millimole, L is understood to be liter, mL is understood to be milliliter, Kg is understood to be kilogram and g be gram, psi is understood to be pound-force per square inch, and mmHg is understood to be millimeters (mm) of mercury (Hg). IFF as used in the examples is understood to mean International Flavors & Fragrances Inc., New York, N.Y., USA.

Example I

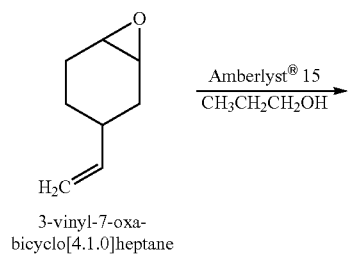

3-vinyl-7-oxa-bicyclo[4.1.0]heptane

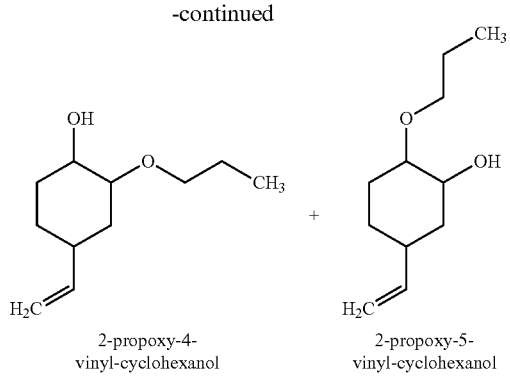

2-propoxy-4-vinyl-cyclohexanol 2-propoxy-5-vinyl-cyclohexanol

Preparation of 2-Propoxy-4-vinyl-cyclohexanol (Structure 29) and 2-Propoxy-5-vinyl-cyclohexanol (Structure 30)

A 5-L, 4-neck round bottom flask was fitted with a temperature probe, a glass stir shaft, a water condenser and an addition funnel Propanol (CH3CH2CH2OH) (1.4 Kg) and Amberlyst® 15 (15 g) were charged into the flask and brought to reflux. 3-Vinyl-7-oxa-bicyclo[4.1.0]heptane (476 g, 3.8 mol) was fed in over 1 hour. The reaction was aged for additional 6 hours and then cooled to room temperature. The reaction mixture was decanted to provide a mixture of 2-propoxy-4-vinyl-cyclohexanol (Structure 29) and 2-propoxy-5-vinyl-cyclohexanol (Structure 30) (1:1) (699 g).

$^1$H NMR (CDCl$_3$, 400 MHz): 5.78-5.90 (m, 1H), 4.94-5.15 (m, 2H), 3.06-3.79 (m, 4H), 2.46-2.58 (m, 1H), 2.34-2.45 (m, 1H), 1.80-2.05 (m, 2H), 1.42-1.72 (m, 6H), 0.93 (t, J=7.4 Hz, 3H)

The isomeric mixture Structure 29 and 30 was described as having sweet, spicy and vanilla notes.

Example II

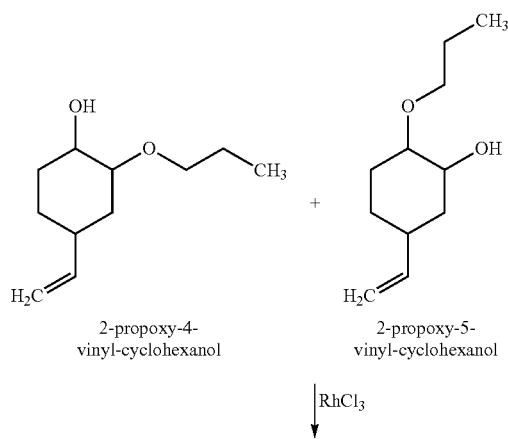

2-propoxy-4-vinyl-cyclohexanol 2-propoxy-5-vinyl-cyclohexanol

|RhCl$_3$

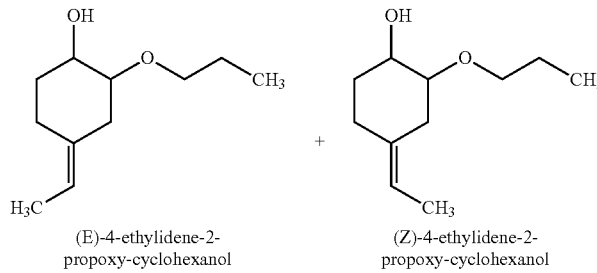
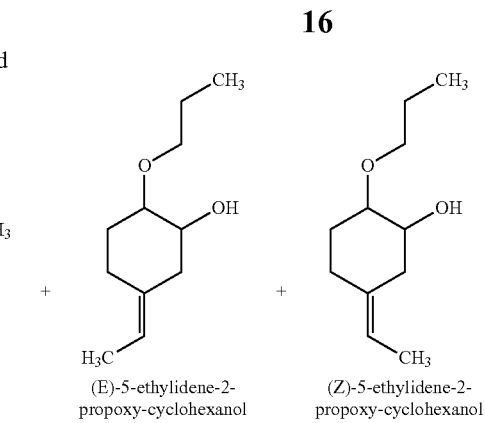

(E)-4-ethylidene-2-propoxy-cyclohexanol (Z)-4-ethylidene-2-propoxy-cyclohexanol (E)-5-ethylidene-2-propoxy-cyclohexanol (Z)-5-ethylidene-2-propoxy-cyclohexanol Preparation of (E)-4-Ethylidene-2-propoxy-cyclohexanol (Structure 17), (Z)-4-Ethylidene-2-propoxy-cyclohexanol (Structure 18), (E)-5-Ethylidene-2-propoxy-cyclohexanol (Structure 19) and (Z)-5-Ethylidene-2-propoxy-cyclohexanol (Structure 20)

The mixture of 2-propoxy-4-vinyl-cyclohexanol (Structure 29) and 2-propoxy-5-vinyl-cyclohexanol (Structure 30) (699 g) (prepared as above in Example I) and $RhCl_3$ (2.0 g, 9.6 mmol) were combined in a fresh 5-L, 4-neck round bottom flask fitted with a temperature probe, a glass stir shaft and a Dean-Stark trap. The reaction mixture was heated to reflux. About 600 mL propanol was removed via the Dean-Stark trap during the reaction. The reaction mixture was aged at reflux for additional 5 hours. Gas chromatography (GC) analysis was used to monitor the completion of the reaction. The reaction mixture was then cooled. Further distillation at a vapor temperature of 123° C. with a pressure of 2 mmHg provided the mixture of (E)-4-ethylidene-2-propoxy-cyclohexanol (Structure 17), (Z)-4-ethylidene-2-propoxy-cyclohexanol (Structure 18), (E)-5-ethylidene-2-propoxy-cyclohexanol (Structure 19) and (Z)-5-ethylidene-2-propoxy-cyclohexanol (Structure 20) (Structure 17:Structure 18:Structure 19:Structure 20=about 0.74:0.83:0.95:1.0) (575 g, 79% yield).

The mixture of (E)-4-ethylidene-2-propoxy-cyclohexanol (Structure 17), (Z)-4-ethylidene-2-propoxy-cyclohexanol (Structure 18), (E)-5-ethylidene-2-propoxy-cyclohexanol (Structure 19) and (Z)-5-ethylidene-2-propoxy-cyclohexanol has the following NMR spectral characteristics:

$^1$H NMR ($CDCl_3$, 500 MHz): 5.14-5.34 ppm (m, 1H), 1.66-3.68 ppm (m, 10H), 1.52-1.66 ppm (m, 5H), 1.09-1.34 ppm (m, 1H), 0.88-1.02 ppm (m, 3H)

The isomeric mixture Structure 17, 18, 19 and 20 was described as having particularly desirable, strong and complex sweet, spicy, woody and vanilla notes.

(E)-4-Ethylidene-2-propoxy-cyclohexanol (Structure 17) has the following NMR spectral characteristics:

$^1$H NMR ($CDCl_3$, 500 MHz): 5.22-5.30 ppm (m, 1H), 3.57-3.64 ppm (m, 1H), 3.51-3.57 ppm (m, 1H), 3.30-3.40 ppm (m, 2H), 2.92-3.03 ppm (m, 1H), 2.67 ppm (br, 1H), 2.47-2.64 ppm (m, 2H), 2.02-2.10 ppm (m, 1H), 1.86-1.94 ppm (m, 1H), 1.66-1.78 ppm (m, 1H), 1.56-1.66 ppm (m, 5H), 1.19-1.29 ppm (m, 1H), 0.94 (t, 3H, J=7.41 Hz)

(E)-4-Ethylidene-2-propoxy-cyclohexanol was described as having spicy, clove-leaf, floral and medicinal notes.

(Z)-4-Ethylidene-2-propoxy-cyclohexanol (Structure 18) has the following NMR spectral characteristics:

$^1$H NMR ($CDCl_3$, 500 MHz): 5.25-5.32 ppm (m, 1H), 3.62-3.70 ppm (m, 1H), 3.50-3.62 ppm (m, 1H), 3.31-3.43 ppm (m, 1H), 2.95-3.03 ppm (m, 2H), 2.66 ppm (br, 1H), 2.13-2.20 ppm (m, 1H), 1.98-2.08 ppm (m, 2H), 1.55-1.66 ppm (m, 6H), 1.23-1.34 ppm (m, 1H), 0.96 ppm (t, 3H, J=7.41 Hz)

(Z)-4-Ethylidene-2-propoxy-cyclohexanol was described as having spicy, clove-leaf and medicinal notes.

(E)-5-Ethylidene-2-propoxy-cyclohexanol (Structure 19) has the following NMR spectral characteristics:

$^1$H NMR ($CDCl_3$, 500 MHz): 5.23-5.30 ppm (m, 1H), 3.56-3.64 ppm (m, 1H), 3.41-3.47 ppm (m, 1H), 3.33-3.39 ppm (m, 1H), 3.13-3.20 ppm (m, 1H), 2.58 ppm (br, 1H), 2.48-2.60 ppm (m, 2H), 2.02-2.10 ppm (m, 2H), 1.67-1.78 ppm (m, 1H), 1.55-1.67 ppm (m, 5H), 1.11-1.21 ppm (m, 1H), 0.94 ppm (t, 3H, J=7.41 Hz)

(E)-5-Ethylidene-2-propoxy-cyclohexanol was described as having balsamic, sweet, spicy and vanilla notes.

(Z)-5-Ethylidene-2-propoxy-cyclohexanol (Structure 20) has the following NMR spectral characteristics:

$^1$H NMR ($CDCl_3$, 500 MHz): 5.25-5.36 ppm (m, 1H), 3.57-3.64 ppm (m, 1H), 3.32-3.43 ppm (m, 2H), 3.13-3.20 ppm (m, 1H), 2.86-2.93 ppm (m, 1H), 2.66 ppm (br, 1H), 2.17-2.23 ppm (m, 1H), 1.96-2.10 ppm (m, 2H), 1.76-1.84 ppm (m, 1H), 1.56-1.67 ppm (m, 5H), 1.13-1.24 ppm (m, 1H), 0.94 ppm (t, 3H, J=7.41 Hz)

(Z)-5-Ethylidene-2-propoxy-cyclohexanol was described as having spicy, clove-leaf, medicinal and slight cooling herbal notes.

Example III

Following cyclohexanols were similarly prepared.

(E)-4-Ethylidene-2-methoxy-cyclohexanol (Structure 1), (Z)-4-Ethylidene-2-methoxy-cyclohexanol (Structure 2), (E)-5-Ethylidene-2-methoxy-cyclohexanol (Structure 3) and (Z)-5-Ethylidene-2-methoxy-cyclohexanol (Structure 4)

$^1$H NMR ($CDCl_3$, 400 MHz): 5.15-5.43 (m, 1H), 3.32-3.62 (m, 4H), 1.94-3.14 (m, 6H), 1.67-1.94 (m, 1H), 1.48-1.67 (m, 3H), 1.08-1.37 (m, 1H)

The isomeric mixture of Structure 1, 2, 3 and 4 was described as having balsamic, sweet, spicy, fruity, fresh and minty notes.

(E)-4-Ethylidene-2-ethoxy-cyclohexanol (Structure 5), (Z)-4-Ethylidene-2-ethoxy-cyclohexanol (Structure 6), (E)-5-Ethylidene-2-ethoxy-cyclohexanol (Structure 7) and (Z)-5-Ethylidene-2-ethoxy-cyclohexanol (Structure 8)

$^1$H NMR (CDCl$_3$, 400 MHz): 5.16-5.38 (m, 1H), 3.32-3.85 (m, 3H), 2.12-3.25 (m, 4H), 1.84-2.11 (m, 2H), 1.64-1.84 (m, 1H), 1.48-1.64 (m, 3H), 1.04-1.34 (m, 4H)

The isomeric mixture of Structure 5, 6, 7 and 8 was described as having strong and complex sweet, spicy, fruity, woody, clove-leaf, floral, green, smoky and leathery notes.

(E)-4-Ethylidene-2-isopropoxy-cyclohexanol (Structure 21), (Z)-4-Ethylidene-2-isopropoxy-cyclohexanol (Structure 22), (E)-5-Ethylidene-2-isopropoxy-cyclohexanol (Structure 23) and (Z)-5-Ethylidene-2-isopropoxy-cyclohexanol (Structure 24)

$^1$H NMR (CDCl$_3$, 400 MHz): 5.18-5.33 (m, 1H), 3.65-3.85 (m, 1H), 2.96-3.57 (m, 2H), 1.87-2.95 (m, 5H), 1.63-1.87 (m, 1H), 1.50-1.63 (m, 3H), 1.07-1.36 (m, 7H)

The isomeric mixture of Structure 21, 22, 23 and 24 was described as having sweet, spicy, woody and vanilla notes.

2-Methoxy-4-vinyl-cyclohexanol (Structure 25) and 2-Methoxy-5-vinyl-cyclohexanol (Structure 26)

$^1$H NMR (CDCl$_3$, 500 MHz): 5.73-5.92 (m, 1H), 4.94-5.14 (m, 2H), 3.67-3.83 (m, 1H), 3.38 (s, 3H), 3.01-3.29 (m, 1H), 2.37-2.60 (m, 2H), 1.79-2.03 (m, 2H), 1.44-1.68 (m, 4H)

The isomeric mixture of Structure 25 and 26 was described as having fruity, vanilla and green notes.

2-Ethoxy-4-vinyl-cyclohexanol (Structure 27) and 2-Ethoxy-5-vinyl-cyclohexanol (Structure 28)

$^1$H NMR (CDCl$_3$, 500 MHz): 5.74-5.96 (m, 1H), 4.95-5.17 (m, 2H), 3.07-3.77 (m, 4H), 2.47-2.57 (m, 1H), 2.18-2.45 (br, 1H), 1.78-2.06 (m, 2H), 1.42-1.72 (m, 4H), 1.20 (t, J=6.9 Hz, 3H)

The isomeric mixture of Structure 27 and 28 was described as having spicy and vanilla notes. 2-Isopropoxy-4-vinyl-cyclohexanol (Structure 35) and 2-Isopropoxy-5-vinyl-cyclohexanol (Structure 36):

$^1$H NMR (CDCl$_3$, 400 MHz): 5.68-5.95 (m, 1H), 4.89-5.16 (m, 2H), 3.16-3.83 (m, 3H), 2.70-2.86 (m, 1H), 2.41-2.61 (m, 1H), 1.73-1.98 (m, 2H), 1.43-1.73 (m, 4H), 1.10-1.22 (m, 6H)

The isomeric mixture of Structure 35 and 36 was described as having a spicy note.

2-Butoxy-4-vinyl-cyclohexanol (Structure 37) 2-Butoxy-5-vinyl-cyclohexanol (Structure 38)

$^1$H NMR (CDCl$_3$, 400 MHz): 5.68-5.95 (m, 1H), 4.91-5.14 (m, 2H), 3.04-3.80 (m, 4H), 2.41-2.66 (m, 2H), 1.79-2.05 (m, 2H), 1.44-1.73 (m, 6H), 1.31-1.44 (m, 2H), 0.92 (t, J=7.3 Hz, 3H)

The isomeric mixture of Structure 37 and 38 was described as having sweet and spicy notes.

2-Isobutoxy-4-vinyl-cyclohexanol (Structure 39) and 2-Isobutoxy-5-vinyl-cyclohexanol (Structure 40)

$^1$H NMR (CDCl$_3$, 400 MHz): 5.72-5.98 (m, 1H), 4.86-5.14 (m, 2H), 3.56-3.83 (m, 1H), 3.06-3.40 (m, 3H), 2.41-2.63 (m, 2H), 1.74-2.00 (m, 3H), 1.44-1.73 (m, 4H), 0.85-0.95 (m, 6H)

The isomeric mixture of Structure 39 and 40 was described as having onion- and garlic-like notes.

Example IV

Additional hydrogenated cyclohexanols were prepared via the hydrogenation of the corresponding cyclohexanols prepared in the above.

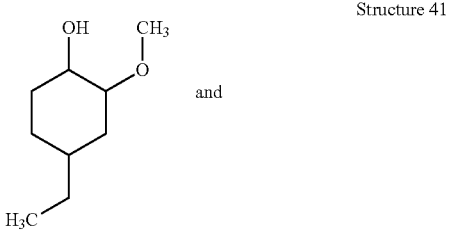

Structure 41

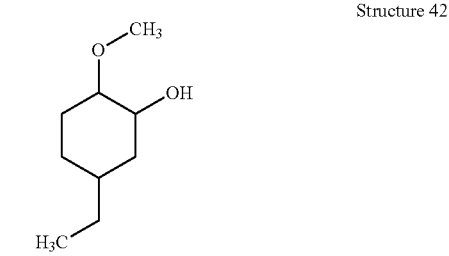

Structure 42

4-Ethyl-2-methoxy-cyclohexanol (Structure 41) and 5-Ethyl-2-methoxy-cyclohexanol (Structure 42)

$^1$H NMR (CDCl$_3$, 500 MHz): 3.57-3.74 (m, 1H), 3.38 (s, 3H), 3.02-3.21 (m, 1H), 2.32 (br, s, 1H), 1.74-1.89 (m, 2H), 1.59-1.68 (m, 1H), 1.39-1.55 (m, 4H), 1.26-1.35 (m, 2H), 0.87-0.92 (m, 3H)

The isomeric mixture of Structure 41 and 42 was described as having spicy and vanilla but phenolic notes.

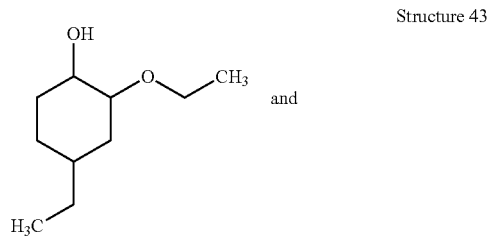

Structure 43

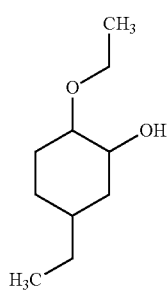

4-Ethyl-2-ethoxy-cyclohexanol (Structure 43) and
5-Ethyl-2-Ethoxy-cyclohexanol (Structure 44)

$^1$H NMR (CDCl$_3$, 500 MHz): 2.96-3.78 (m, 4H), 2.50 (br, s, 1H), 1.96-2.13 (m, 1H), 1.57-1.88 (m, 2H), 1.36-1.57 (m, 2H), 1.08-1.36 (m, 6H), 0.77-1.04 (m, 4H)

The isomeric mixture of Structure 43 and 44 was described as having earthy, woody and green but phenolic notes.

Structure 45

Structure 46

4-Ethyl-2-propoxy-cyclohexanol (Structure 45) and
5-Ethyl-2-propoxy-cyclohexanol (Structure 46)

$^1$H NMR (CDCl$_3$, 400 MHz): 2.91-3.92 (m, 5H), 1.06-2.16 (m, 11H), 0.72-1.03 (m, 6H)

The isomeric mixture of Structure 45 and 46 was described as having spicy and vanilla but phenolic notes.

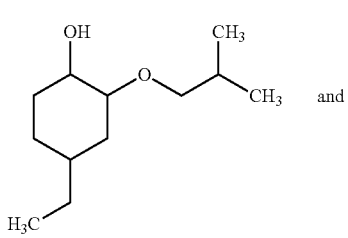

Structure 47

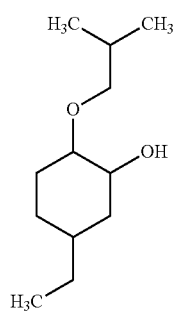

4-Ethyl-2-isobutoxy-cyclohexanol (Structure 47)
and 5-Ethyl-2-isobutoxy-cyclohexanol (Structure 48)

$^1$H NMR (CDCl$_3$, 400 MHz): 2.58-3.76 (m, 5H), 1.00-2.14 (m, 10H), 0.77-1.00 (m, 9H)

The isomeric mixture of Structure 47 and 48 was described as having spicy and woody notes with bacon character.

Accordingly, the novel cyclohexanols represented by Formula I-VI possess unexpected superior and desirable effect when compared to their corresponding hydrogenated compounds.

What is claimed is:

1. A method of improving, enhancing or modifying a fragrance formulation through the addition of an olfactory acceptable amount of a compound of formula:

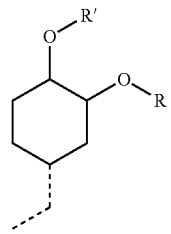

an isomer or a mixture of isomers thereof,
wherein one of R and R' represents hydrogen with the other representing a C$_1$-C$_6$ linear, branched, or cyclic alkyl, alkenyl, alkynyl or aromatic group; and
one of the dashed lines represents a carbon-carbon single bond with the other representing a carbon-carbon double bond.

2. The method of claim 1, wherein in the compound is a compound of formula:

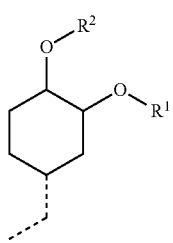

an isomer or a mixture of isomers thereof,
wherein one of R¹ and R² represents hydrogen with the other representing a $C_1$-$C_6$ linear, branched or cyclic alkyl group; and
one of the dashed lines represents a carbon-carbon single bond with the other representing a carbon-carbon double bond.

3. The method of claim 1, wherein the compound is a compound of formula:

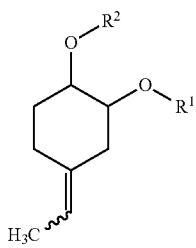

an isomer or a mixture of isomers thereof,
wherein one of R¹ and R² represents hydrogen with the other representing a $C_1$-$C_6$ linear, branched or cyclic alkyl group.

4. The method of claim 3, wherein the compound is selected from the group consisting of (E)-4-Ethylidene-2-methoxy-cyclohexanol;
(Z)-4-Ethylidene-2-methoxy-cyclohexanol;
(E)-5-Ethylidene-2-methoxy-cyclohexanol;
(Z)-5-Ethylidene-2-methoxy-cyclohexanol;
(E)-4-Ethylidene-2-ethoxy-cyclohexanol;
(Z)-4-Ethylidene-2-ethoxy-cyclohexanol;
(E)-5-Ethylidene-2-ethoxy-cyclohexanol;
(Z)-5-Ethylidene-2-ethoxy-cyclohexanol;
(E)-4-Ethylidene-2-propoxy-cyclohexanol;
(Z)-4-Ethylidene-2-propoxy-cyclohexanol;
(E)-5-Ethylidene-2-propoxy-cyclohexanol;
(Z)-5-Ethylidene-2-propoxy-cyclohexanol;
(E)-4-Ethylidene-2-isopropoxy-cyclohexanol;
(Z)-4-Ethylidene-2-isopropoxy-cyclohexanol;
(E)-5-Ethylidene-2-isopropoxy-cyclohexanol;
(Z)-5-Ethylidene-2-isopropoxy-cyclohexanol; and
a mixture thereof.

5. The method of claim 1, wherein the olfactory acceptable amount is from about 0.005 to about 50 weight percent of the fragrance formulation.

6. The method of claim 1, wherein the olfactory acceptable amount is from about 0.5 to about 25 weight percent of the fragrance formulation.

7. The method of claim 1, wherein the olfactory acceptable amount is from about 1 to about 10 weight percent of the fragrance formulation.

* * * * *